US012768674B2

(12) United States Patent
Öztürk et al.

(10) Patent No.: US 12,768,674 B2
(45) Date of Patent: Oct. 20, 2026

(54) ENERGY SAVING CAPACITANCE MEASURING CIRCUIT WITH CONTACT AND POSITION DETECTION

(71) Applicant: INOFAB SAGLIK TEKNOLOJILERI ANONIM ŞIRKETI, Çankaya (TR)

(72) Inventors: Merthan Öztürk, Çankaya (TR); Kerem Yasar, Çankaya (TR); Ahmet Oguz, Çankaya (TR); Selim Yonet, Çankaya (TR); Ceren Yavuz, Çankaya (TR); Ilayda Altun, Çankaya (TR); Alper Saraç, Çankaya (TR); Alperen Aktaş, Çankaya (TR); Necdet Can Sonmez, Çankaya (TR); Cagkan Karaarslan, Çankaya (TR)

(73) Assignee: INOFAB SAGLIK TEKNOLOJILERI ANONIM SIRKETI, Ankara (TR)

( * ) Notice: Subject to any disclaimer, the term of this patent is extended or adjusted under 35 U.S.C. 154(b) by 103 days.

(21) Appl. No.: 18/724,868

(22) PCT Filed: Dec. 23, 2022

(86) PCT No.: PCT/TR2022/051588
§ 371 (c)(1),
(2) Date: Jun. 27, 2024

(87) PCT Pub. No.: WO2023/129048
PCT Pub. Date: Jul. 6, 2023

(65) Prior Publication Data

US 2025/0076087 A1 Mar. 6, 2025

(30) Foreign Application Priority Data

Dec. 28, 2021 (TR) .......................... TR2021/021486
Dec. 23, 2022 (TR) .......................... TR2022/020203

(51) Int. Cl.
*G01D 5/24* (2006.01)
*A61M 11/00* (2006.01)

(52) U.S. Cl.
CPC ............... *G01D 5/24* (2013.01); *A61M 11/00* (2013.01); *A61M 2205/13* (2013.01); *A61M 2205/3327* (2013.01)

(58) Field of Classification Search
None
See application file for complete search history.

(56) References Cited

U.S. PATENT DOCUMENTS 10,953,168 B2 3/2021 Biswas et al.
11,058,833 B2 7/2021 Holtz et al.
(Continued)

FOREIGN PATENT DOCUMENTS

TR 202015247 A2 11/2020

OTHER PUBLICATIONS

International Search Report (PCT/ISA/210) and Written Opinion (PCT/ISA/237) mailed on Jun. 19, 2023 by the Turkish Patent Office as the International Searching Authority for International Application No. PCT/TR2022/051588. (7 pages).
(Continued)

*Primary Examiner* — Jas A Sanghera
(74) *Attorney, Agent, or Firm* — Buchanan Ingersoll & Rooney PC

(57) ABSTRACT

The present disclosure relates to a capacitance measuring circuit with contact and position detection for measuring the capacitance used during contact detection and position detection. The object of the present disclosure relates to the development of an electronic circuit that measures the capacitance to be used to track the access of the user to any electronic device, drug, or any machine. Another object of the disclosure is to activate the circuit that provides capaci-
(Continued)

Figure 1:
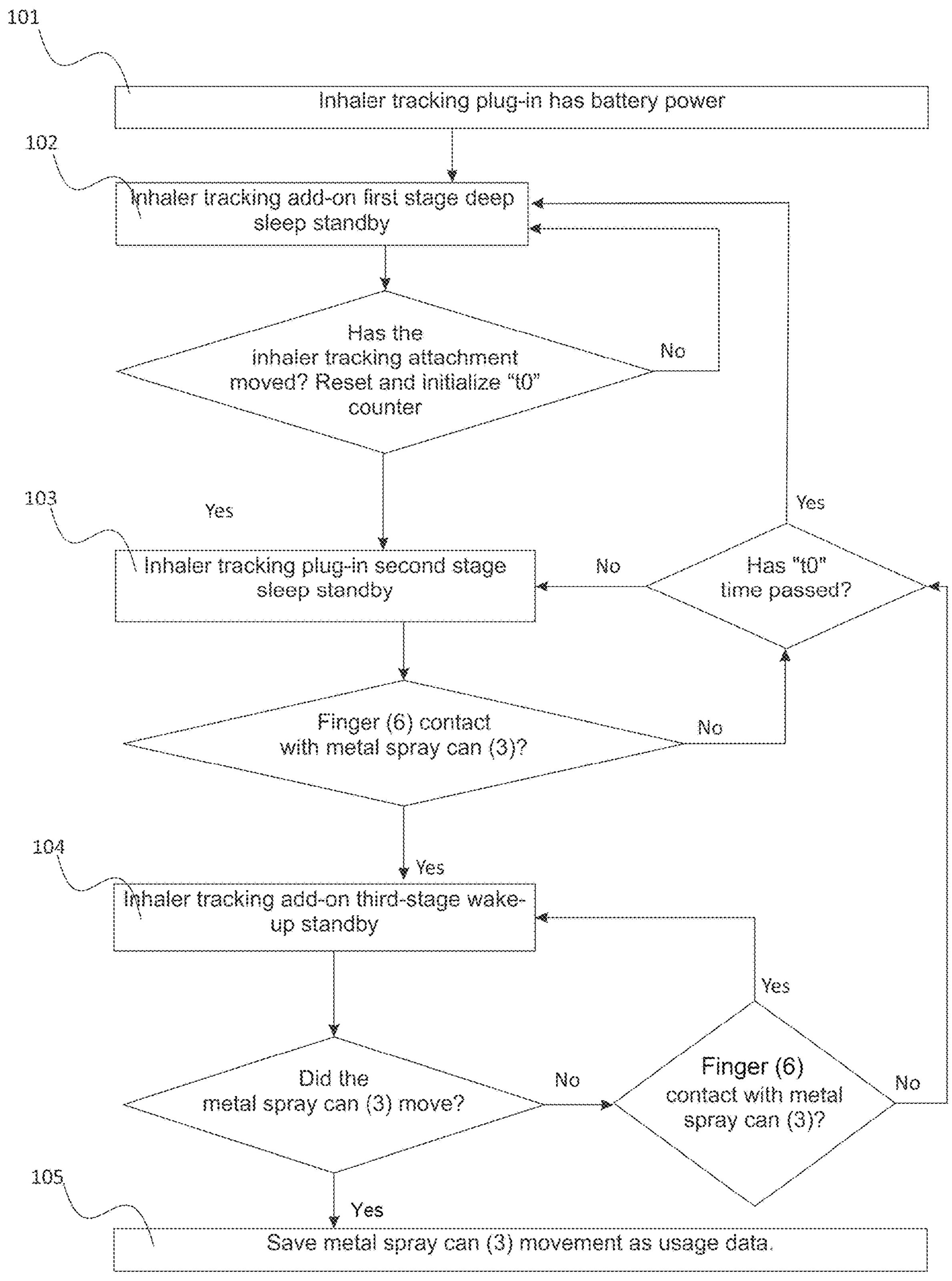

tance measurement with the electrode array that allows the precise position and position detection by changing the capacitance measurement method for allowing the detection of contact with the device. In addition, it is aimed to follow the contact and location measurement sequentially by changing the capacitance measurement approach periodically to track whether the contact with the device continues or not.

6 Claims, 6 Drawing Sheets

(56) References Cited

U.S. PATENT DOCUMENTS

| | | | | |
|---|---|---|---|---|
| 2015/0174348 | A1 | 6/2015 | Tunnell et al. | |
| 2016/0144141 | A1* | 5/2016 | Biswas ............... | A61M 15/009 128/200.23 |
| 2019/0125990 | A1 | 5/2019 | Holtz et al. | |
| 2020/0155775 | A1 | 5/2020 | Keppner et al. | |
| 2021/0205550 | A1 | 7/2021 | Biswas et al. | |
| 2021/0298124 | A1 | 9/2021 | Hatton et al. | |
| 2022/0357184 | A1 | 11/2022 | Yasar et al. | |

OTHER PUBLICATIONS

Extended European Search Report issued on Jan. 30, 2026, in corresponding European Patent Application No. 22917048.5. (11 pages).

* cited by examiner

ENERGY SAVING CAPACITANCE MEASURING CIRCUIT WITH CONTACT AND POSITION DETECTION

TECHNICAL FIELD

The present invention relates to a contact and position sensing capacitance measuring circuit to be used for capacitance measurement during contact with the metal spray canister and position detection in the actuator.

BACKGROUND

Switches are used to start, shut down, and change the operating parameters of electronic devices. The opening and closing of these switches can be accomplished by triggering the electronic or electromechanical switch circuits with digital signals as well as by the users playing a mechanical sequence of components. One of the switch types used to detect user contact is the system that measures capacitance. These systems generate a signal by detecting the changing capacitance value as a result of the contact with the user's conductive hand. This signal can be used to open, close or record any circuit.

When the first examples of touch-screen mobile phones based on capacitance measurement were released in 2007 (for example, Apple's iPhone 3G model), the device could not detect on-screen touch when the screen was turned off. After the user pressed a mechanical switch, the capacitance measurement system, which tracks finger movements on the screen, was also activated when the screen was displayed. Capacitance measurement for detecting finger contact on the screen without the need for any mechanical switch to open the screen is continuously performed on many phones produced in 2015 and later (for example, Apple's iPhone X model) and finger contact is understood thanks to the sudden decrease in capacitance value. After this finger detection, the display on the screen of the mobile device is realized thanks to the software of the device.

An invention developed to detect user contact by measuring capacitance is described in the United States Patent application US2019125990. The present invention is based on the detection of this contact if the user contacts the capacitance sensor by measuring the capacitance. As a result of this contact, the moments when the user accesses his medication or medical device can be recorded. Since the process of sensing contact with capacitance measurement causes a very low level of electricity consumption, it is possible to record every moment of contact with small battery support for long periods.

THE OBJECT OF THE INVENTION

The object of the present invention relates to the development of an electronic circuit that measures the capacitance to be used to track the access of the user to any electronic device, drug, or any machine. Another object of the invention is to activate the circuit that provides capacitance measurement with the electrode array that allows the precise position and position detection by changing the capacitance measurement method that allows the detection of contact with the device. In addition, it is aimed to follow the contact and location measurement sequentially by changing the capacitance measurement approach periodically to track whether the contact with the device continues or not.

DEFINITIONS OF FIGURES DESCRIBING THE INVENTION

The figures and related descriptions used to better explain the capacitance measurement system developed by this invention are as follows.

FIG. 1 A progressive wake-up algorithm of the inhaler capacitance measurement circuit.

Figure 2:
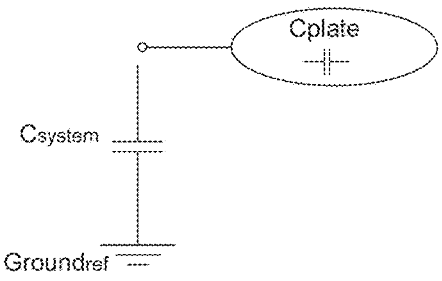

FIG. 2 An example view of the electronic circuit diagram of the capacitance measurement system.

Figure 3:
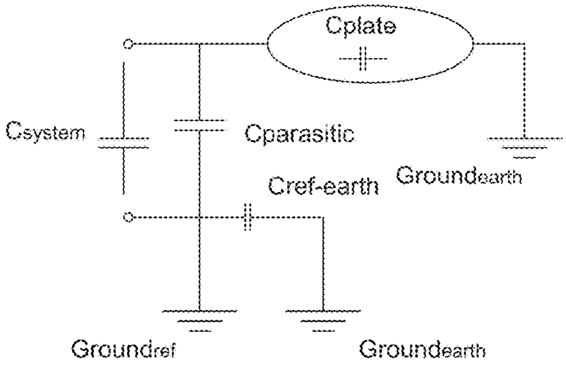

FIG. 3 A view of the Cparasitic and Cref-earth added version of the electronic circuit diagram of the capacitance measurement system seen in FIG. 2.

Figure 4:
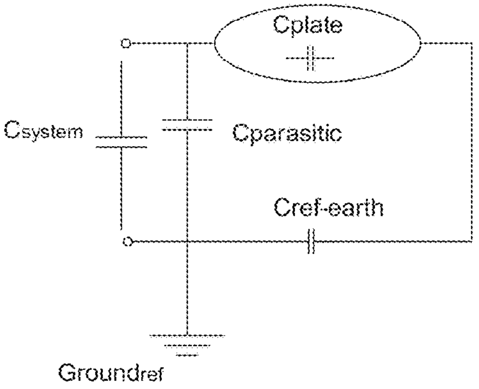

FIG. 4 A unified view of the $\text{Ground}_{earth}$ lines of the electronic circuit diagram of the capacitance measurement system shown in FIG. 3.

Figure 5:
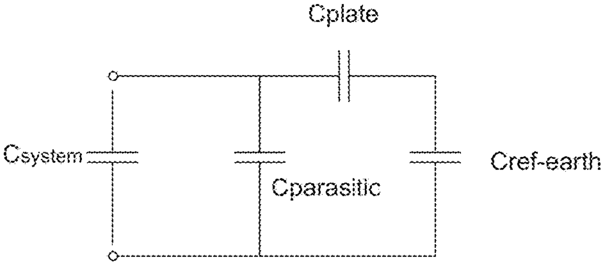

FIG. 5 A view of the simplified electronic circuit diagram of the capacitance measurement system shown in FIG. 4.

Figure 6:
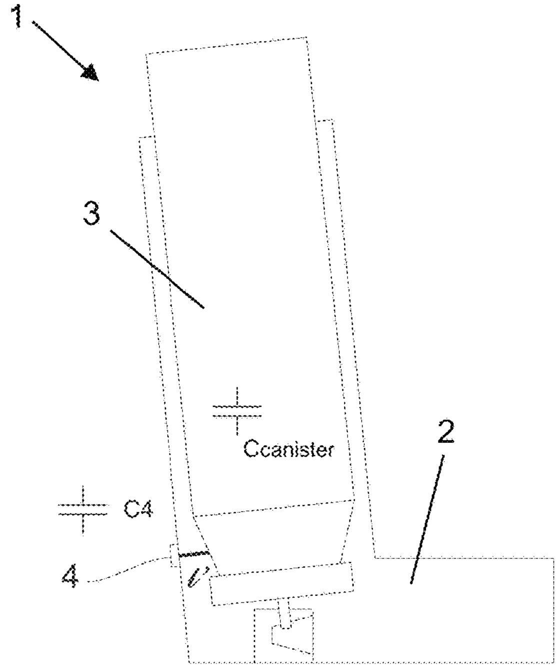

FIG. 6 A schematic view of the layout of the systems measuring the capacitance values of the inhaler actuator when the sectioned version of the inhaler actuator is not in contact with the metal spray canister.

Figure 7:
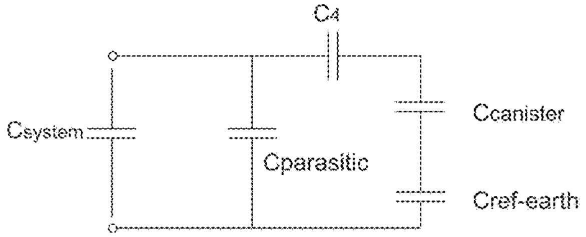

FIG. 7 A view of the capacitance measurement electronic circuit scheme when the inhaler is not in contact with the metal spray canister.

Figure 8:
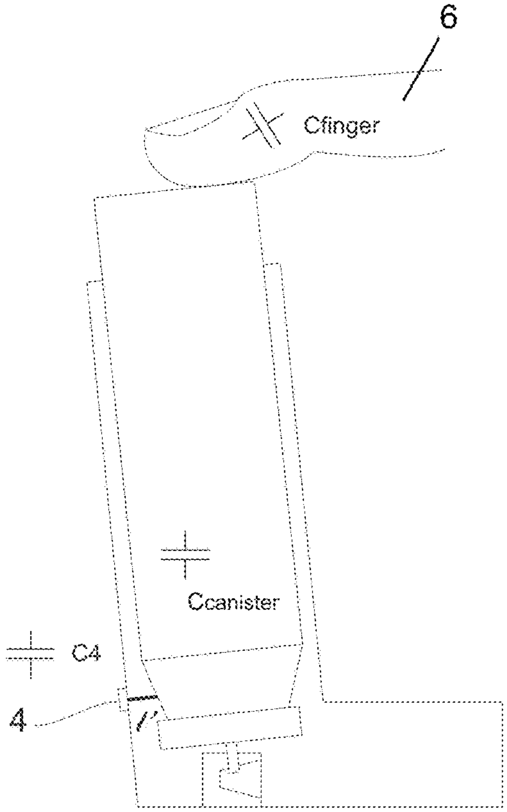

FIG. 8 A schematic view of the layout of the systems measuring the capacitance values of the inhaler actuator in the case of contact with the metal spray canister.

Figure 9:
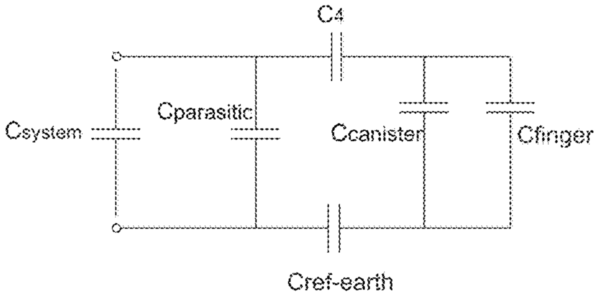

FIG. 9 A view of the capacitance measurement electronic circuit scheme when the inhaler is in contact with the metal spray canister.

Figure 10:
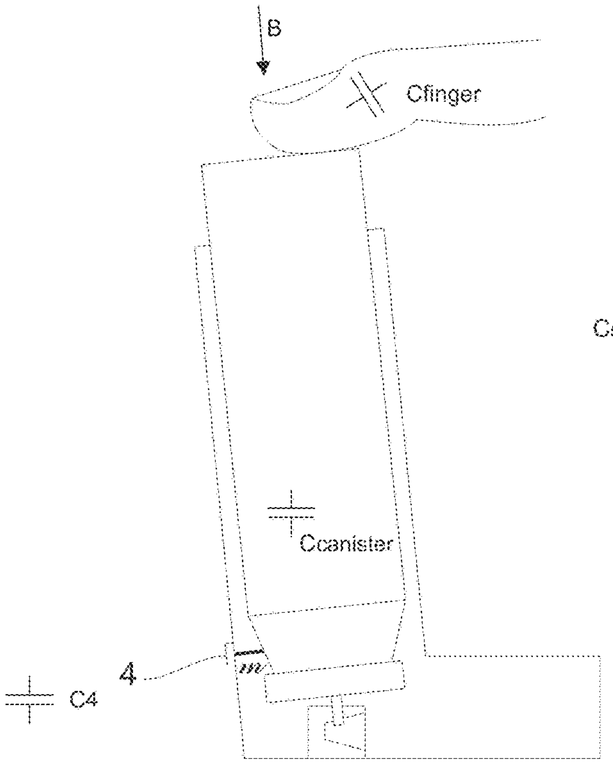

FIG. 10 A schematic view of the systems measuring the capacitance values when the inhaler actuator is contacted with the metal spray canister in cross-section and the pressure force (B) and the metal spray canister are pushed into the actuator.

Figure 11:
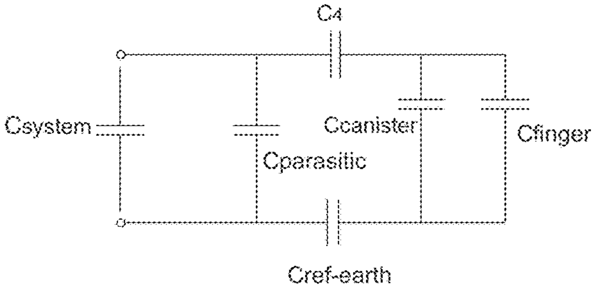

FIG. 11 A view of the capacitance measurement electronic circuit diagram where the inhaler is contacted with the metal spray canister and the metal spray canister is pushed into the actuator by the pressure force (B).

Figure 12:
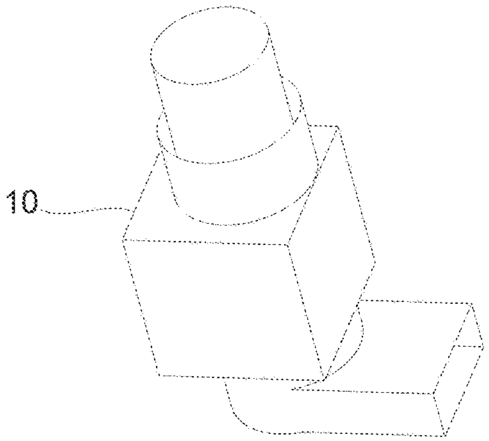

FIG. 12 A schematic view of the inhaler's actuator in which the attachment containing the electronic system of the invention is placed.

Figure 13:
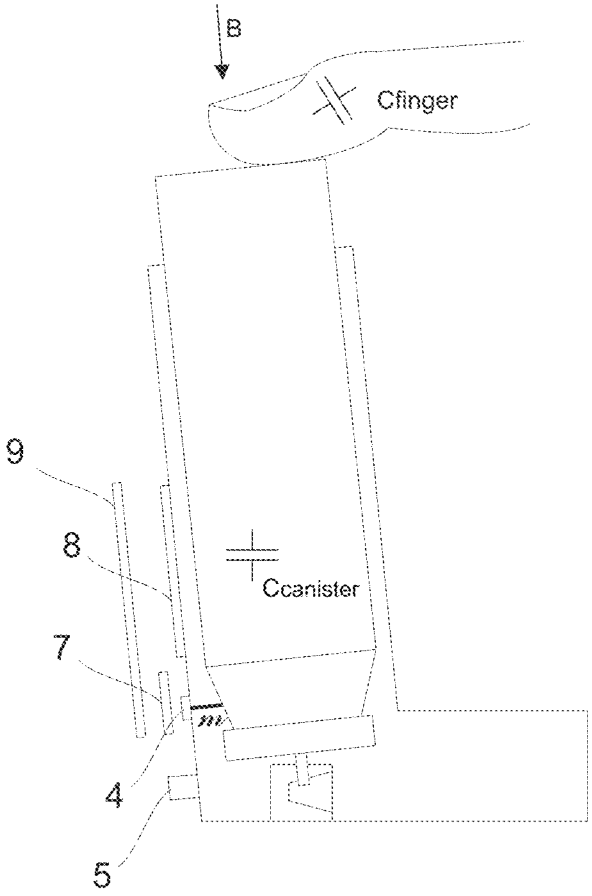

FIG. 13 A schematic view of the layout of the systems measuring the capacitance values of the inhaler actuator when the metal spray canister is contacted in section and the pressure force (B) and the metal spray canister are pushed into the actuator.

Figure 14:
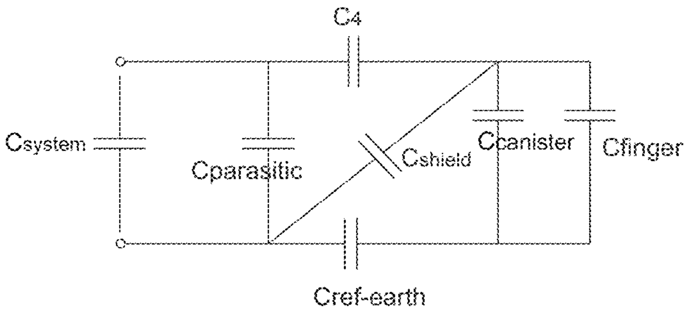

FIG. 14 A view of the capacitance measurement electronic circuit diagram where the inhaler is contacted with the metal spray canister and the metal spray canister is pushed into the actuator by the pressure force (B).

Figure 15:
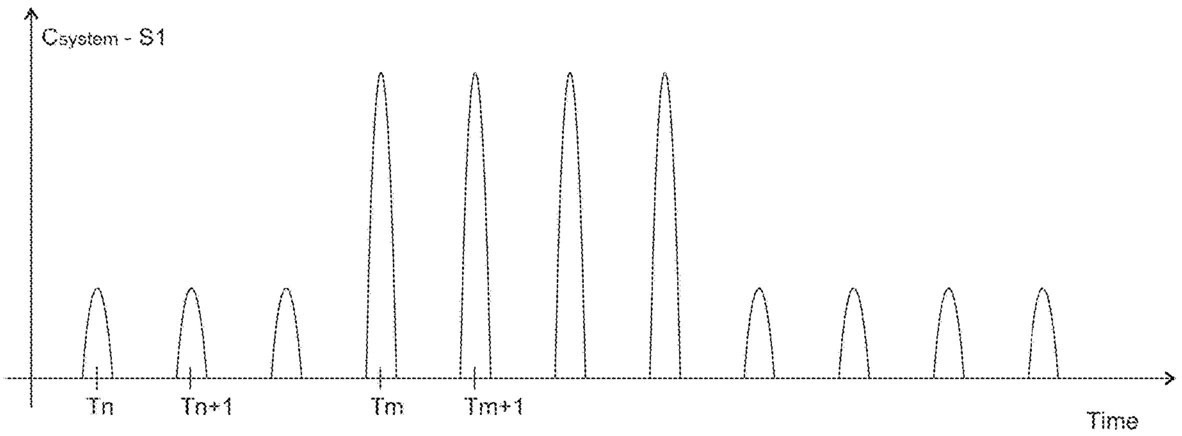

FIG. 15 A graph schematically showing the measurements made by the capacitance measurement system, which checks whether there is finger contact with the metal spray canister, at a certain frequency and the change of the capacitance value measurement results obtained by 4 according to the time and capacitance value.

Figure 16:
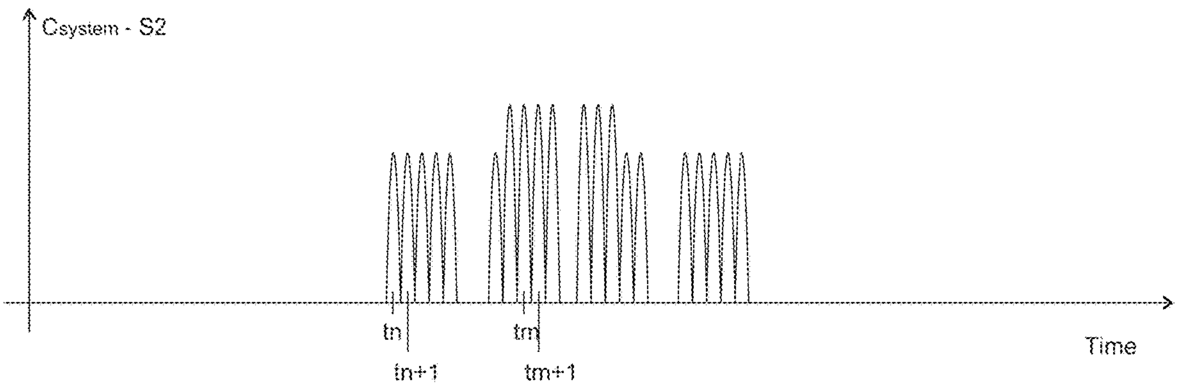

FIG. 16 A graph schematically showing the measurements made by the capacitance measurement system at a certain frequency and the change of the capacitance value measurement results obtained according to the time and capacitance value, which checks whether the metal spray canister is pushed after finger contact to the metal spray canister.

Figure 17:
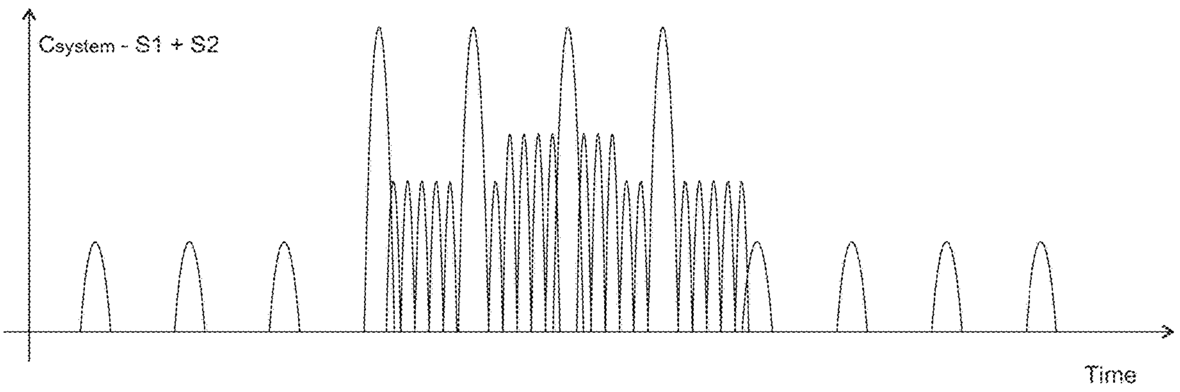

FIG. 17 A graph schematically showing the measurements made by two different measurement circuits of the capacitance measurement system, which checks whether there is finger contact in the metal spray canister and whether the metal spray canister is moving, and the capacitance value obtained according to the time and capacitance value.

DEFINITIONS OF ELEMENTS OF THE INVENTION

The electronic devices and components in which an exemplary application of the capacitance measurement accuracy improvement circuit is made are shown in the accompanying figures.

The parts and sections in these figures are numbered and the corresponding of each number is given below.

1. Inhaler
2. Plastic actuator
3. Metal spray canister
4. Capacitance sensor
5. Switch
6. Finger
7. Active voltage follower shield ($C_{shield}$)
8. Variable plate
9. Reference ground ($Ground_{ref}$)
10. Inhaler tracking attachment

DETAILED DESCRIPTION OF THE INVENTION

The inhaler (1) consists of a plastic actuator (2) made of plastic and a metal spray canister (3) that enters it. If the metal spray canister (3) is shaken before each use and then pressed into the plastic actuator (2), the amount of medicine sprayed is the same for each use. The inhaler tracking attachment (10), which is operated with battery energy that is passed/inserted outside the actuator to monitor the frequency of drug use and to record each use, will ensure that the usage record is kept without restricting the use of the inhaler (1).

Electronic devices switch themselves to energy conservation status to reduce their energy consumption and are opened after the user's demand for use in many different ways in terms of energy efficiency. It is one of the frequently used methods for devices that use batteries to automatically turn on their screens and start switch lighting after detecting that they will be used thanks to their sensors (microphone, vibration sensor, accelerometer, gyroscope, proximity sensor, capacitance sensor, etc.) that monitor ambient variability.

The inhaler tracking attachment (10) of the invention will be in a 3-stage awake state during the battery power period (101) and the electronic components operating at each different stage will be operated in different circuit driving modes. In the preferred embodiment of the invention, these stages and circuit component driving modes are described in the following order. These are as follows;

First Stage Deep Sleep State

In the first stage deep sleep state, one or more of the following components for motion detection will be open:

accelerometer and/or
gyroscope and/or
vibration sensor.

At this stage, the motion measurement component will be driven in sparse mode. In the preferred embodiment of the invention, the motion sensing accelerometer will be driven at a value between 0.2-100 Hz, preferably 1.6 Hz, during the sparse mode.

Second Stage Sleep State

In the second stage sleep state, one or more of the following components for motion detection will be run accelerometer and/or
gyroscope and/or
vibration sensor, and
capacitance sensor (4).

Capacitance sensor (4) will be operated in "finger (6) contact measurement mode" to detect whether there is finger (6) contact only with the metal spray canister (3) at this stage. The motion measurement component, which operates in the first stage deep sleep state and switches to the second stage, will be driven in frequent mode. In the preferred embodiment of the invention, the motion sensing accelerometer will be driven at a value between 1-1000 Hz, preferably 16 Hz during the frequent mode.

Third Stage Awake State

In the third stage awake state, one or more of the following components for motion detection will be run;

accelerometer and/or
gyroscope and/or
vibration sensor, and capacitance sensor (4).

The capacitance sensor (4) is capable of detecting the movement of the metal spray canister (3) as well as detecting situations where there is contact with the finger (6). For this, however, it will be necessary to change the operating mode and switch to "metal spray canister (3) motion measurement mode". During the motion measurement mode, if the physical distance of the metal spray canister (3) to the capacitance sensor (4) increases/decreases, the increasing/decreasing capacitance value can be measured.

The following shows a list of open and closed circuit components and their open/closed state in all stages.

| Component-State | First Stage Deep Sleep | Second Stage Sleep | Third Stage Awake | Third Stage Awake |
|---|---|---|---|---|
| Staying in Stage Requirement | Always open | Open for 10 seconds after motion detection | Intermittent open in the case of Contact Detection | Intermittent open in the case of Contact Detection |
| Accelerometer/gyroscope/vibration sensor | Open 0.2-100 Hz preferably 1.6 Hz | Open 1-1000 Hz, preferably 12.5 Hz | Open 1-1000 Hz, preferably 12.5 Hz | Open 1-1000 Hz, preferably 26 Hz |
| Capacitance sensor (Metal spray canister contact detection) | Closed In order to keep the mean capacitance of 1/30 Hz up to date | Open 1-1000 Hz, preferably 2.5 Hz | Open 1-1000 Hz, preferably 2.5 Hz | Closed |

-continued

| Component-State | First Stage Deep Sleep | Second Stage Sleep | Third Stage Awake | Third Stage Awake |
|---|---|---|---|---|
| Capacitance sensor (Metal spray canister motion detection) | Closed | Closed | Closed | Open 1-1000 Hz, preferably 20 Hz |

Working Detail of Contact and Motion Detection Algorithm to Metal Spray Canister The circuit of the inhaler tracking attachment (10) will continuously remain in the first stage of deep sleep (102). The movements and/or contacts regarding whether the inhaler (1) will be used during the first stage awake state will be monitored. If the user moves an inhaler (1) in the table, bag, or pocket, this situation can be detected with the help of an accelerometer or similar sensor through the inhaler tracking attachment (10). After this determination, the inhaler tracking attachment (10) will go into the second stage sleep state for the period of "$t_0$" (103).

In the second stage sleep state, the inhaler tracking attachment (10) can monitor whether the metal spray canister (3), which is a component of the inhaler (1), has been contacted by the user or not, thanks to the capacitance value of this metal spray canister (3). Because the capacitance value of this component will change in case of contact, for this purpose, contact detection capacitance measurement will be initiated to monitor the contact of the metal spray canister (3) with the finger (6) (104).

If the user does not have a finger (6) contact with the metal spray canister (3), the inhaler tracking attachment (10) will return to the first stage deep sleep. If finger (6) contact occurs, the inhaler tracking attachment (10) will switch to the third stage awake state (105).

In the third stage awake state, the capacitance sensor (3) will be driven like two different circuits thanks to a switch element, allowing two different measurements to be made one after the other at different time intervals. First of all, the contact detection will be determined through the capacitance measurement circuit whether the user's finger (6) contact continues for the predefined "t1" period.

If this "t1" period has elapsed, capacitance measurement will be initiated to monitor the movement of the metal spray canister (3). In order to move the metal spray canister (3), it will be necessary to press the metal spray canister (3) into the plastic actuator (2) by applying more pressure without cutting the contact of the finger (6). At this stage, since the capacitance value of the metal spray canister (3) in contact with the finger (6) is already very high, the circuit drive will be changed to see whether there is movement in the metal spray canister (3) for a period of "t2".

If the metal spray canister does not move during the "t2" period, the metal spray canister (3) will be subjected to the step of examining whether the contact continues. If the movement of the metal spray canister (3) is detected, this situation will be recorded as usage data. After these stages, the inhaler tracking attachment (10) will proceed to the first stage deep sleep standby state (102) step.

It will be ensured that the first, second, and third stage sleep and transition to awake states are awakened by a new part of the electronic circuit at each later stage. In the decreasing stages, unnecessary circuit elements will be put to sleep. Energy saving will be achieved in this way. Since sensor components with low energy consumption will be continuously open during awakening between stages, they will be placed in the front rows so that other components can be awakened, while components with high energy consumption will be placed in the next rows for subsequent awakening. Sensors such as vibration sensors, accelerometers, and gyros with low energy consumption can be used to switch from deep sleep to sleep stage.

A capacitance measurement circuit that can measure the capacitance from one or more points after the capacitance measurement sensor circuit is awakened will begin to measure the system capacitance value ($C_{system}$).

Thanks to the monitoring of the capacitance value ($C_{system}$) of the system, it can be understood that the user contacts the finger (6) with the metal spray canister (3). After it is understood that the inhaler (1) will be used after the user touches the metal spray canister (3), another awakening will be made and the third stage will start to be awake. After the awakening, the usage tracking attachment (10) will be enabled to create a record.

This record may only include the time when the user has come into contact with the inhalers (1), as well as records of further steps of pressing, shaking, breathing, or exhalation. Components such as a microphone, vibration sensor, accelerometer, gyroscope, and proximity sensor can be used to determine the conditions of pressing the metal spray canister (3), shaking the inhaler (1), and breathing and exhaling into it. In addition, it can be ensured that any of these sensors start to perform capacitance measurement monitoring periodically for a limited period in case of second stage sleep and/or third stage awake state and/or for the capacitance sensor (4) to detect the contact with the metal spray canister (3).

Various sensors can make the first awakening erroneously since the inhaler (1) is walking in the pocket, while carrying it in the bag, or moving in any means. After the awakening, after the inhaler tracking attachment (10) detects that there is no contact with the metal spray canister (3) through the capacitance sensor (4), it will be ensured that the capacitance sensor (4) turns off and remains in a first stage deep sleep state again. In order to reduce the frequency of such erroneous awakening, the amount of erroneous awakening can be reduced over time by detecting a patient-specific motion pattern from patient movements with data from microphones, vibration sensors, accelerometers, gyroscopes, proximity sensors by artificial intelligence-based learning.

Understanding the user's finger (6) contact will be used for the transition of the electronic circuit to the third stage awake state, and the initiation of the energy consuming circuit elements such as the display, sensor, and wireless communication modules will take place after the awakening. Finger (6) contact is inevitable as MDI (Metered Dose Inhaler) products require contact with the metal spray canister (3) and even pressing. With the pressure of the finger (6), it is ensured that the metal spray canister (3) entering the plastic actuator (2) can spray. The amount of movement of the metal spray canister (3) in the plastic actuator (2) is necessary for the metal spray canister (3) to spray a certain amount of medicine.

The capacitance measurement circuit of the invention performs the capacitance measurement in an electronic device called an inhaler tracking attachment (10) powered by a battery. For this reason, instead of using the ground line accessible through wall sockets, it uses the ground line formed by electronic cards and electronic components as the reference ground ($Ground_{ref}$) (9). All conductive surfaces used during the capacitance measurement, all conductive electronic circuit elements, even the circuit board itself, will have a certain capacitance "$C_{ref\text{-}earth}$" value relative to the circuit's reference ground line ($Ground_{ref}$) (9) and the earth's ground line ($Ground_{earth}$). Monitoring and participation in the calculations of the capacitance values of all components in the circuit are necessary to calculate the capacitance change created by an external contact finger (6). If the measurement of the capacitance value ($C_{plate}$) of any plate is to be made with a portable device using batteries, the value of "$C_{ref\text{-}earth}$" and the parasitic capacitance value "Cparasitic" of the system will also have to be taken into account.

In FIG. 2, the circuit diagram of the equivalent capacitance value ($C_{system}$) of a plate suspended in the air is shown in FIG. 5. The transformation of the circuit is schematically shown in FIGS. 3-4, respectively.

The body of the metal spray canister (3) is made of aluminum, which is a conductive material, and both show a change in capacitance with the contact of the finger (6) and creates a change in the measured capacitance values (C4) if the metal spray canister (3) approaches or moves away from at least one capacitance sensor (4) with the pressure (B) of the finger (6). Thanks to the observation of this change, it can be understood whether the metal spray canister (3) is moving.

If it is desired to observe only the movements of the metal spray canister (3), it will be sufficient to compare the values measured through the capacitance sensor (4). However, the differences between these values cause very small value differences due to the high capacitance value ($C_{system}$) of the system during the detection of the first contact. Because the effect of capacitance changes depending on the "l" and "m'" positions before and after the finger (6) pressure (B) of the C4 capacitance values will be very low against the capacitance value ($C_{finger}$) of the finger (6) and the capacitance value ($C_{canister}$) of the metal spray canister (3), which are the other elements of the series-connected circuit (FIG. 8, 10, or 13).

In order to change the amount of these two capacitance values in order to reduce the capacitance value ($C_{finger}$) of the finger (6) and the capacitance value ($C_{canister}$) of the metal spray canister (3), the changes in C4 capacitance values will be observed separately and thanks to the switch that directs the circuit to the active voltage follower shield (7) (FIG. 13).

The active voltage follower shield (7) ($C_{shield}$) wraps the circumference of the metal spray canister (3) over the plastic actuator (2). In order to detect the movement of the metal spray canister while the circuit is awake, a large capacitance value will be reached when the circuit is driven with the ground value. The active voltage follower shield (7) ($C_{shield}$) changes the circuit connection by moving a two-way switch circuit to the S1 (Switch-1) or S2 (Switch-2) positions during its connection to the circuit. Accordingly, When the Switch Circuit is in the S1 Position: The active voltage follower shield (7) is loaded equally to the potential value on the capacitance sensor (4) so that ($C_{shield}$) does not occur. In this way, it does not appear on the circuit because it does not create an additional capacitance value on the circuit.

When the Switch Circuit is in the S2 Position: The active voltage follower shield (7) ($C_{shield}$) allows serial connection to these two components to reduce the effect of the capacitance value ($C_{finger}$) of the finger (6) and the capacitance value ($C_{canister}$) of the metal spray canister (3) to detect the high one due to the finger (6) contact.

When the switch circuit is in the S1 position, the $C_{system}$ measurements are made at each $T_n$ time of the system capacitance value. The ΔT value may be between 0.5-5 seconds or it is determined as 1 second in the preferred application of the invention. Accordingly, $$\Delta T = T_{n+1} - T_n \cong 1 \text{ Second}$$

Every 1 second, the $C_{system}$ value is measured when the switch circuit is in the S1 position to check that there is finger (6) contact with the metal spray canister (3). If a $C_{system}$ value higher than the mean of the last 2-20 values is measured, it will be assumed that the user is in finger contact.

When the switch circuit is in the S2 position, the measurements are made at each $t_n$ time of the system capacitance value $C_{system}$. The Δt value may be between 5-500 milliseconds and it is determined as 50 milliseconds in the preferred application of the invention. Accordingly, $$\Delta t = t_{n+1} - t_n \cong 50 \text{ ms}$$

As mentioned above, the $C_{system}$ value is measured every 1 second when the switch circuit is in the S1 position to check for finger (6) contact with the metal spray canister (3). If finger (6) is detected in the S1 position, the switch position will be switched to S2 and the $C_{system}$ value will be measured by switching to S1 again to check whether the contact of the finger (6) continues at the end of ΔT. If the finger (6) contact continues, it will be ensured that the switch will switch back to the S2 position and the process will be repeated by waiting for ΔT.

If a higher $C_{system}$ value is measured than the mean of the values taken at any time with the Δt time intervals in which the switch is located in each S2 position, the user will be deemed to have displaced the metal spray canister (3).

It has been mentioned that changes can be observed by taking the mean of the last $C_1$, $C_2$, $C_3$, . . . $C_n$ values to monitor the variability to be made by looking at the difference between the mean of the previous values and ($C_{mean}$) of the capacitance value measurements. In addition, a calculation method that consumes fewer resources can be used to determine the differences as follows instead of storing the last 2-20 values. Accordingly, $$C_{mean} = C_{mean-1} + \left(\frac{C_n}{X} - \frac{C_{mean-1}}{X}\right)$$

In the above equation, the "X" value can be changed between 2-100 according to the expectation of fast or slow observation of the change effect.

In order for the capacitance measurements made in contact with and moving the metal spray canister (3) to create noticeable effects, the active voltage follower shield (7) and the reference ground (9), which are among the circuit components, will not be located in the electrical contact, and physical distance will be created between them in order not to affect each other. This distance will be at least 0.1 mm for the circuit operating voltage such as 0-5V. With the increase of the circuit operating voltage, it will be ensured that the said physical distance value will be increased.

In the absence of any of the components for motion detection such as accelerometer and/or gyroscope and/or vibration sensor to follow the movements of the inhaler (1), with the capacitance measurement system that only detects the contact of the finger (6) with the canister (3), it is possible to switch from the first stage sleep state to the second stage sleep state.

The invention claimed is:

1. A method for measuring a capacitance used during contact detection and position detection in an inhaler tracking attachment, the method comprising:

while the inhaler tracking attachment is on battery power, remaining in a first stage deep sleep state;

switching an inhaler from the first stage deep sleep state to a second stage sleep state for a period of "t0" after a user's finger contacts a metal spray canister;

initiation of contact detection capacitance measurement to monitor whether a user is in contact with the metal spray canister, which is a component of the inhaler, with a capacitance value of the metal spray canister to determine that the user's finger is contacting the inhaler through the metal spray canister without the user's finger being moved closer to a capacitance sensor;

in case of contact with the user's finger, switching the capacitance sensor to a third stage awake state, in which a measurement circuit is operated for detecting the contact of the user's finger and for motion tracking of the metal spray canister, the measurement circuit using a switch element with different time intervals, one after the other, such that the measurement circuit is configured to detect the contact of the user's finger based on a first time interval and track the motion of the metal spray canister based on a second time interval, thereby enabling the measurement circuit to operate like two different circuits; and if movement of the metal spray canister is detected, recording the movement as usage data.

2. The method according to claim 1, wherein remaining in the first stage deep sleep state while one or more of motion detection components including an accelerometer and/or a gyroscope and/or a vibration sensor are turned on as long as the inhaler tracking attachment is on the battery power.

3. The method according to claim 2, comprising:

performing the step of switching to the second stage sleep state for the period of "t0" when it is detected that the inhaler has been moved by one or more components for motion detection including at least one of an accelerometer, a gyroscope, and a vibration sensor.

4. The method according to claim 3, comprising:

proceeding to the first stage deep sleep state step after the step of detecting the movement of the metal spray canister and recording the movement as usage data.

5. The method according to claim 1, comprising:

performing a step of separately and clearly observing the changes in the C4 capacitance values using a switch that directs the measurement circuit to be connected in parallel to two capacitances to change a value of the two capacitances in order to reduce an effect of a capacitance value ($C_{finger}$) of the user's finger and a capacitance value ($C_{canister}$) of the metal spray canister in the step of detecting the movement of the metal spray canister in the third stage awake state.

6. An inhaler tracking attachment for measuring a capacitance used during contact detection and position detection, comprising:

a plastic actuator that ensures that an amount of drug sprayed is consistent for each use when a metal spray canister is shaken before each use and then pressed into the plastic actuator, and the metal spray canister entered into the plastic actuator, and a capacitance sensor with one or more components for motion detection including at least one of an accelerometer, a gyroscope, and a vibration sensor; and a switch that directs a measurement circuit to be connected in parallel to two capacitances to change capacitance values of the two capacitances in order to reduce an effect of a capacitance value ($C_{finger}$) of a user's finger and a capacitance value ($C_{canister}$) of the metal spray canister for monitoring changes in the capacitance values of the two capacitances, which are measured when the metal spray canister approaches or moves away from the capacitance sensor, either by contact with the user's finger or by pressure from the user's finger, wherein the metal spray canister is formed of aluminum.

* * * * *